(12) United States Patent
Rife

(10) Patent No.: US 8,389,956 B2
(45) Date of Patent: Mar. 5, 2013

(54) LARYNGOSCOPE DISINFECTOR

(76) Inventor: Robert Rife, Mt. Pleasant, SC (US)

( * ) Notice: Subject to any disclaimer, the term of this patent is extended or adjusted under 35 U.S.C. 154(b) by 37 days.

(21) Appl. No.: 13/197,498

(22) Filed: Aug. 3, 2011

(65) Prior Publication Data

US 2013/0032733 A1 Feb. 7, 2013

(51) Int. Cl.
*A61L 2/10* (2006.01)

(52) U.S. Cl. .................. 250/455.11; 250/504 R; 422/1; 422/22; 422/24

(58) Field of Classification Search ............ 250/504 R, 250/455.11, 492.1; 422/1, 22
See application file for complete search history.

(56) References Cited

U.S. PATENT DOCUMENTS

| | | | |
|---|---|---|---|
| 3,683,638 A | 8/1972 | Devon | |
| 3,936,186 A | 2/1976 | Boland et al. | |
| 5,029,252 A * | 7/1991 | Ameseder | 250/455.11 |
| 5,166,528 A * | 11/1992 | Le Vay | 250/455.11 |
| 5,288,647 A | 2/1994 | Zimlich et al. | |
| 5,597,597 A | 1/1997 | Newman | |
| 5,637,877 A | 6/1997 | Sinofsky | |
| 6,096,264 A * | 8/2000 | Peifer | 422/1 |
| 6,433,343 B1 * | 8/2002 | Cimino et al. | 250/455.11 |
| 6,461,569 B1 | 10/2002 | Boudreaux | |
| 6,565,802 B1 * | 5/2003 | Hanley et al. | 422/22 |
| 6,767,453 B2 | 7/2004 | Lifschitz | |
| 6,911,177 B2 | 6/2005 | Deal | |
| 6,986,867 B2 * | 1/2006 | Hanley et al. | 422/22 |
| 7,459,695 B2 * | 12/2008 | Hanley et al. | 250/455.11 |
| 7,798,159 B2 * | 9/2010 | Palfy et al. | 134/184 |
| 8,203,124 B2 * | 6/2012 | Havens et al. | 250/455.11 |
| 2006/0175554 A1 * | 8/2006 | Riddell | 250/455.11 |
| 2010/0266445 A1 * | 10/2010 | Campagna | 422/23 |
| 2011/0155924 A1 * | 6/2011 | Lo | 250/455.11 |

FOREIGN PATENT DOCUMENTS

| | | |
|---|---|---|
| DE | 292805 | 1/1981 |
| GB | 2364622 | 1/2002 |
| JP | 11009546 | 1/1999 |
| WO | 9953966 | 10/1999 |

* cited by examiner

*Primary Examiner* — Jack Berman
*Assistant Examiner* — Johnnie L Smith
(74) *Attorney, Agent, or Firm* — Barnwell Whaley Patterson & Helms, LLC

(57) ABSTRACT

A laryngoscope disinfector characterized by a drawer that provides positioning for laryngoscopes in the drawer so that all surfaces of the laryngoscopes are exposed to ultraviolet radiation. The drawer provides for the laryngoscope blades to be positioned generally horizontally and generally vertically for disinfection of the blades. The drawer also provides, in some embodiments, positioning for the laryngoscope handles.

10 Claims, 5 Drawing Sheets

LARYNGOSCOPE DISINFECTOR

FIELD OF THE INVENTION

This invention relates to medical devices generally, and is more specifically directed to an ultraviolet disinfector for laryngoscopes.

BACKGROUND OF THE INVENTION

Laryngoscopes in common use are characterized by a handle, with a blade extending from the handle. In most embodiments, the blade is curved, and extends at generally a right angle from the handle. The handle is usually held in a generally vertical orientation. The handle may contain a battery for powering a light source that is present in the laryngoscope blade. The handle may provide light by means of a fiber optic light source. In more sophisticated embodiments, the handle and blade may provide video imaging which appears on a remote monitor.

For laryngoscopes as contemplated by the present invention, the blade may be separated from the handle. Since the blade is inserted through the patient's mouth, it is imperative that the blade is disinfected, and even sterilized, prior to reuse. Laryngoscopes should be thoroughly disinfected.

The use of chemical agents for disinfecting is problematic. Certain bacteria may be resistant to chemical cleaning. It has been demonstrated that ultraviolet radiation, such as ultraviolet-C radiation, is effective in killing bacteria and other harmful pathogens. However, it is important that the ultraviolet light be directed to all surfaces of the laryngoscope, and that certain surfaces are not hidden in shadows, or masked by surfaces of any ultraviolet disinfecting device.

There is a need for a laryngoscope disinfector that uses ultraviolet radiation to disinfect the laryngoscope, and particularly, the laryngoscope blade. There is a need for a device that will provide for all surfaces of the ultraviolet radiation reaching all surfaces of the laryngoscope blade.

SUMMARY OF THE INVENTION

The present invention is a laryngoscope disinfector characterized by a drawer that provides positioning for laryngoscopes in the drawer so that all surfaces of the laryngoscopes are exposed to ultraviolet radiation. The drawer provides for the laryngoscope blades to be positioned generally horizontally and generally vertically for disinfection of the blades. The drawer also provides, in some embodiments, positioning for the laryngoscope handles.

DESCRIPTION OF PREFERRED EMBODIMENTS

Figure 1:
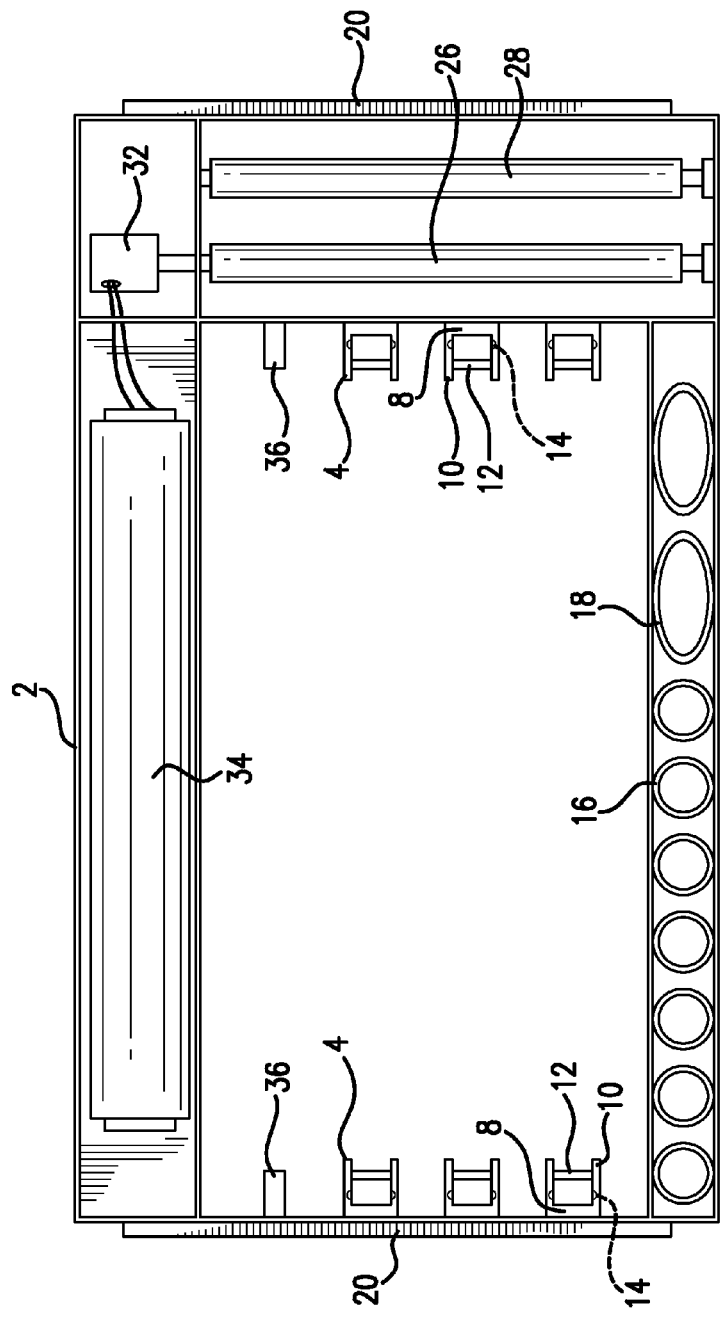
FIG. 1 is a top plan view of a drawer for the laryngoscope disinfector.
Figure 2:
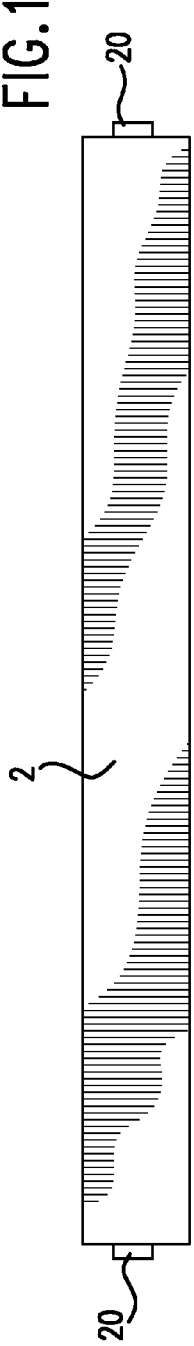
FIG. 2 is a side view of the drawer for the laryngoscope disinfector.
Figure 3:
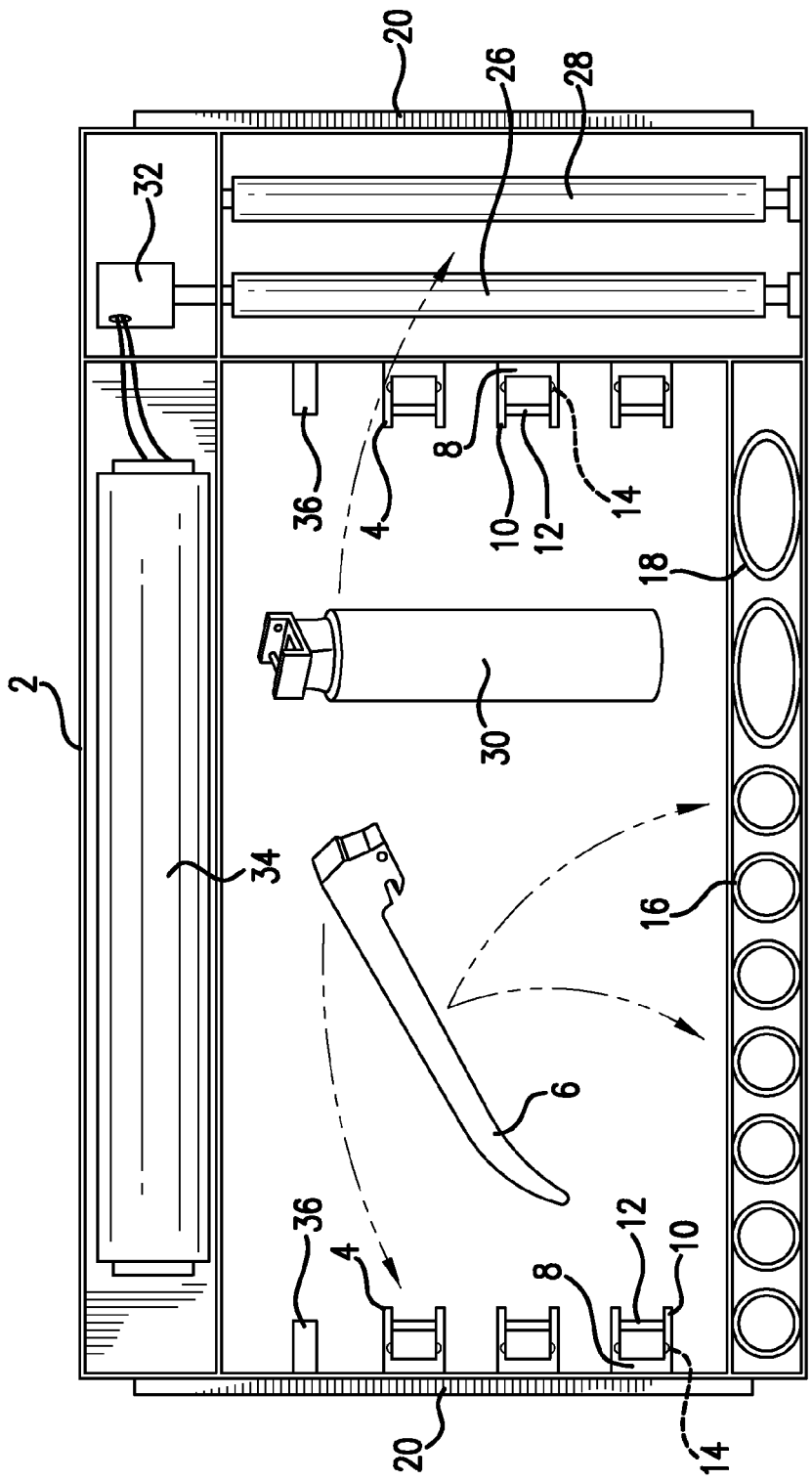
FIG. 3 demonstrates positioning of a laryngoscope blade and a separated laryngoscope handle within the drawer.
Figure 5:
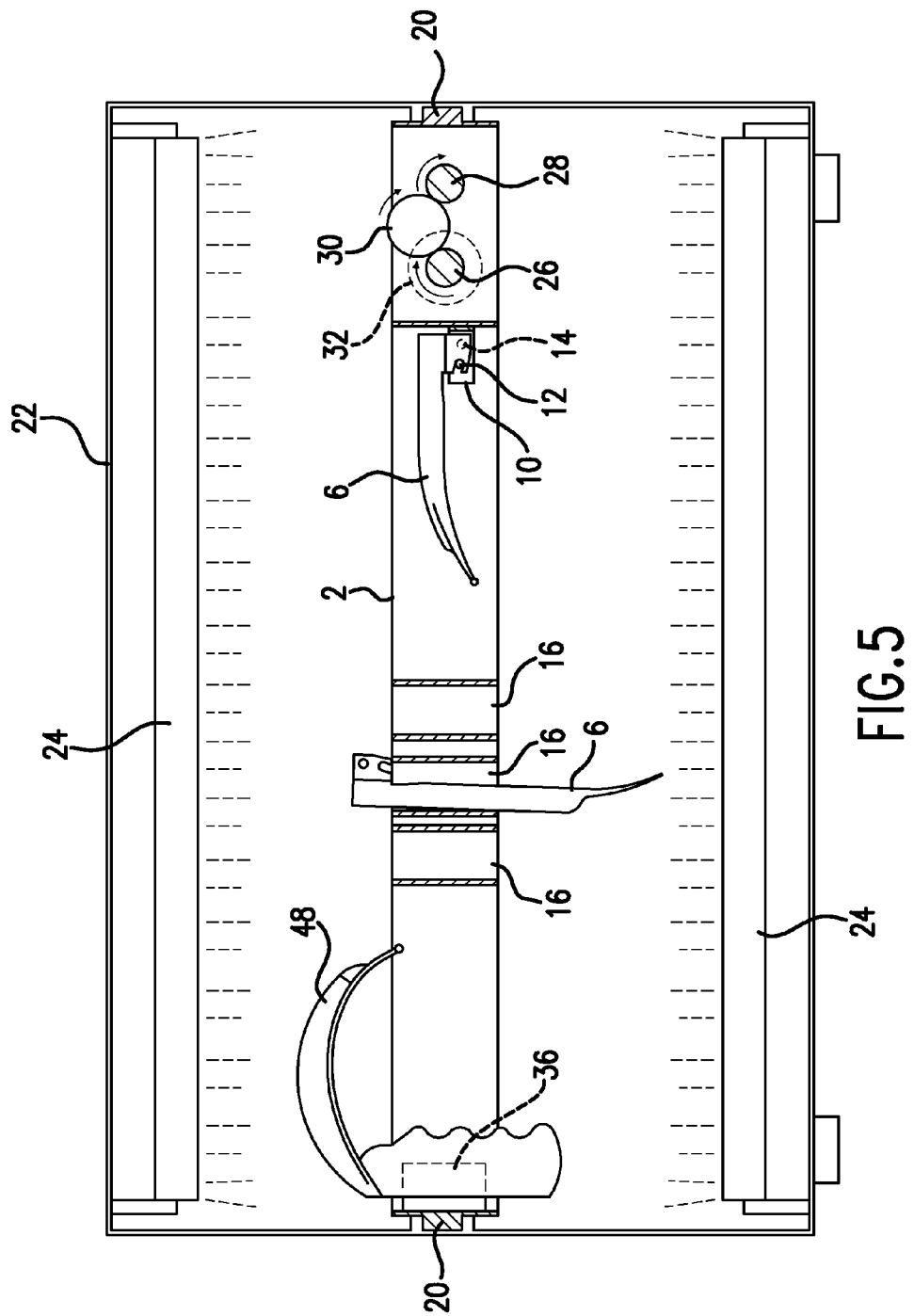
FIG. 5 shows a side view of the drawer with laryngoscope handles in position, and with the drawer mounted in an ultraviolet cabinet, with the drawer shown as a sectioned view taken essentially along line 5-5 of FIG. 4.

Turning now to the drawing figures, a preferred embodiment of the invention is formed as a drawer 2. FIG. 1. The drawer has a plurality of sides that form an annular boundary of the drawer. In a preferred embodiment, the drawer is generally rectangular, and has at least four (4) sides that form the annular drawer. The top and bottom of the drawer are open, that is, there are no barriers to obstruct the transmission of the ultraviolet light, so that ultraviolet light is directed through the drawer from top to bottom or bottom to top, and preferably, in both directions. FIG. 5. Alternatively, the drawer may be formed with a top and/or a bottom; however, the top and/or bottom must be formed of a material that is substantially transparent to ultraviolet radiation and will permit ultraviolet radiation to pass through the material.

Figure 4:
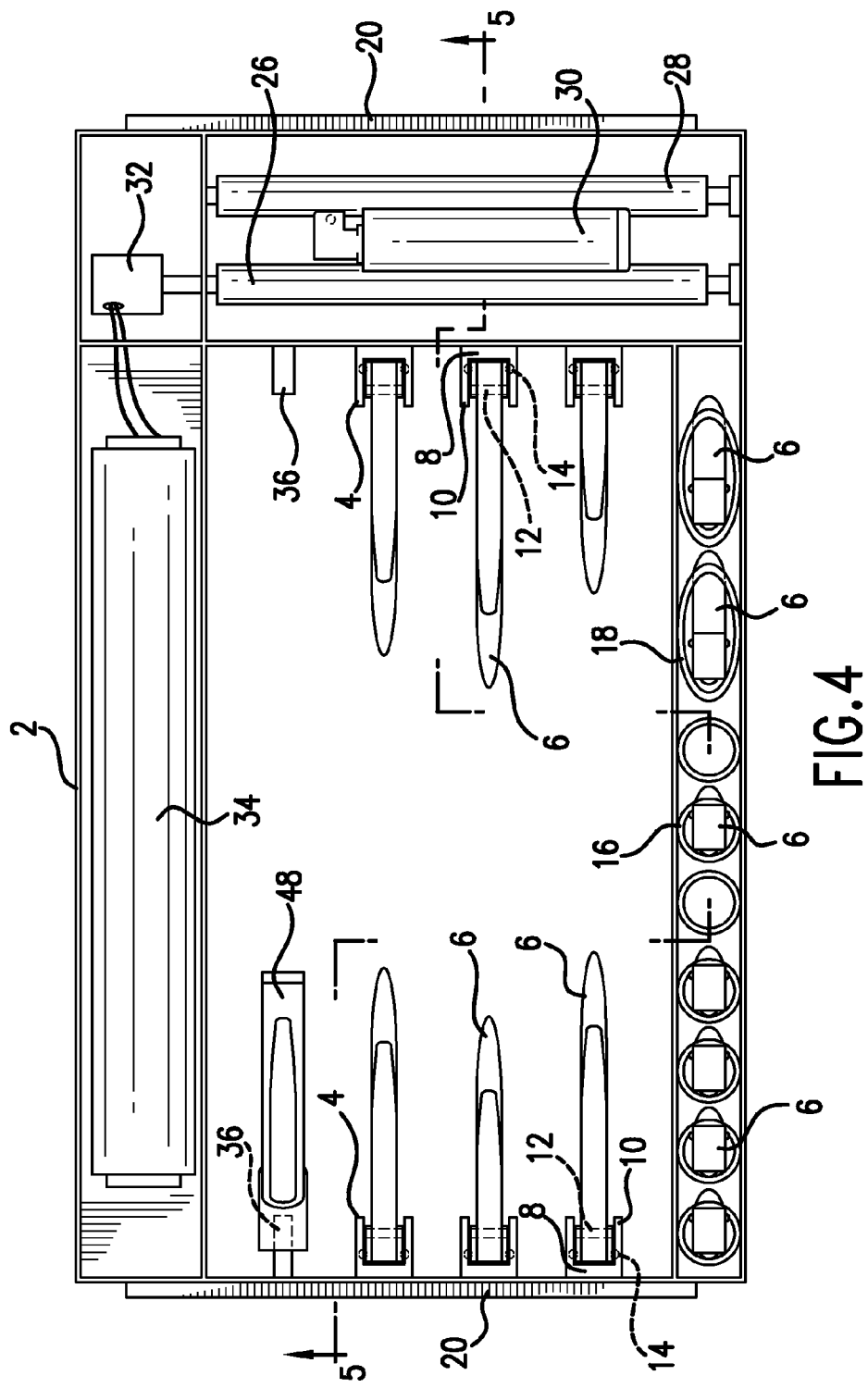
FIG. 4 shows the drawer of FIG. 1, with laryngoscope blades and laryngoscope handles is position in the drawer.

Sides of the drawer may have mounting brackets 4 extending there from as shown in the embodiments of the drawing figures. A plurality of brackets is constructed to accept and hold laryngoscope blades 6 oriented so that the laryngoscope blades extend generally horizontally and toward the center of the drawer. FIG. 4; FIG. 5.

As shown in FIG. 1, in one embodiment there are six (6) mounting brackets, with each bracket characterized by a mounting base 8 having generally parallel arms 10 extending outwardly from the mounting base. A pin 12 is positioned between the spaced apart parallel arms near an end of the base that is distal to the side of the drawer to which the mounting bracket is mounted. An indention 14 is formed in each of the parallel arms and on an interior of the parallel arms. The mounting bracket so constructed receives and holds the laryngoscope blades as shown in FIG. 5. Blades of laryngoscopes may be straight or curved, and of various sizes. The blades may be of various sizes. The mounting brackets and the drawer are constructed and arranged to receive and hold the various blade constructs.

The laryngoscope blades are disinfected by ultraviolet radiation while positioned in the mounting bases as described above, with the laryngoscope blades extending generally horizontally. In this position, a portion of the laryngoscope blade that is connected to the mounting base is masked from receiving radiation.

The drawer provides a plurality of annular voids 16,18. The annular voids allow the laryngoscope to be inserted generally vertically, so that the proximal end of the laryngoscope blade is disinfected by ultraviolet radiation. FIG. 5. The voids may be formed of different sizes and shapes, such as round and/or oval, as shown in the drawing figures. The size and shape is selected and constructed to receive the blade within the void, but the size and shape does not allow the blade to completely pass through the void.

In use, the drawer is positioned in the cabinet as shown in FIG. 5. Sliders 20 may be provided on the drawer that slidably engages the cabinet 22 for sliding the drawer in and out of the cabinet. The laryngoscope blades are disinfected by positioning the blades in the mounting receptacles of the mounting bases, and operating the ultraviolet emitting lamps 24 of the cabinet for a cycle.

The lamps may emit ultraviolet-c radiation. The lamps may be LEDs or elongated lamps or other ultraviolet radiation emitting devices that will effectively kill undesirable pathogens.

The drawer is then partially or fully slidably withdrawn from the cabinet for access to the laryngoscope blades. The laryngoscope blades are repositioned to a generally vertical position within the cabinet, and the ultraviolet lamps are cycled again. The blades may be exposed to ultraviolet radiation in the vertical position, and subsequently repositioned to the generally horizontal holders, and the ultraviolet lams cycled again.

The device also provides for handles of the laryngoscope to be disinfected in some embodiments. As shown, a pair of generally parallel rollers 26, 28 may be provided. The handle 30 of laryngoscope, which is disassembled from the blade, is positioned on the rollers. In one embodiment, roller 26 is connected to a motor 32 that rotates the roller. The frictional engagement of the roller with the handle of the laryngoscope causes rotation of the handle, thereby exposing the handle of the laryngoscope to ultraviolet radiation on all exterior surfaces of the handle, and disinfecting the exterior of the laryngoscope handle.

The motor may be powered by a battery 34. Alternatively, the motor may be powered by current from the cabinet. Contact points on the drawer, or on the sliders for the drawer, may connect with a current source for the cabinet to provide power for the motor.

In another embodiment, a block 36 may extend from a side of the drawer. The block engages a void in a handle of another form of laryngoscope. In this embodiment, the laryngoscope blade and handle are mounted as shown in FIG. 5.

In use, laryngoscope blades and handles may be positioned in the drawer as shown in FIG. 4 and FIG. 5. The drawer is fully inserted into the cabinet. The cabinet should have a door that fully closes the cabinet, to prevent ultraviolet radiation from escaping from the cabinet. The device is then cycled for an appropriate time to disinfect the laryngoscope components that are present in the cabinet. The length of cycle time for the radiation depends upon the strength of the ultraviolet radiation source, and the pathogens which are to be killed by the ultraviolet radiation source.

In one embodiment, the cabinet has walls 38 with enhanced reflectivity. The walls reflect radiation toward the laryngoscope components. Some or all of the walls and interior surfaces may be reflective, such as by applying white or silver paint, or by using mirrored surfaces. Similarly, the interior sides of the drawers may have reflective materials or surfaces that reflect ultraviolet radiation to enhance the efficacy of the device.

In another embodiment, ultraviolet light emitting diodes 40 are positioned within the cabinet. Light emitting diodes typically consume less energy than elongated bulbs of the type shown in FIG. 5. Therefore, light emitting diodes, particularly when placed in a relatively small cabinet as shown in FIG. 6 and FIG. 7, may be powered by a portable battery as a power source.

Figure 6:
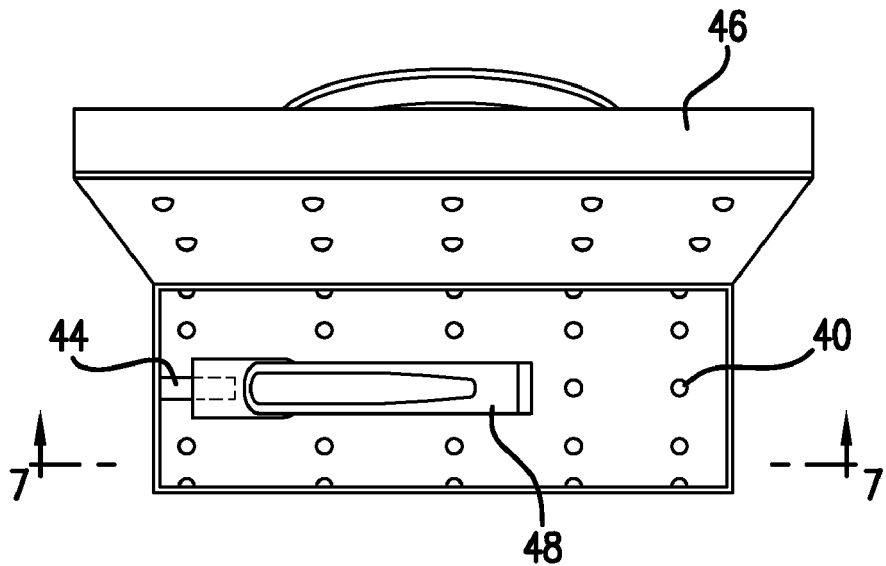
FIG. 6 is a portable laryngoscope disinfector shown in top plan view.
Figure 7:
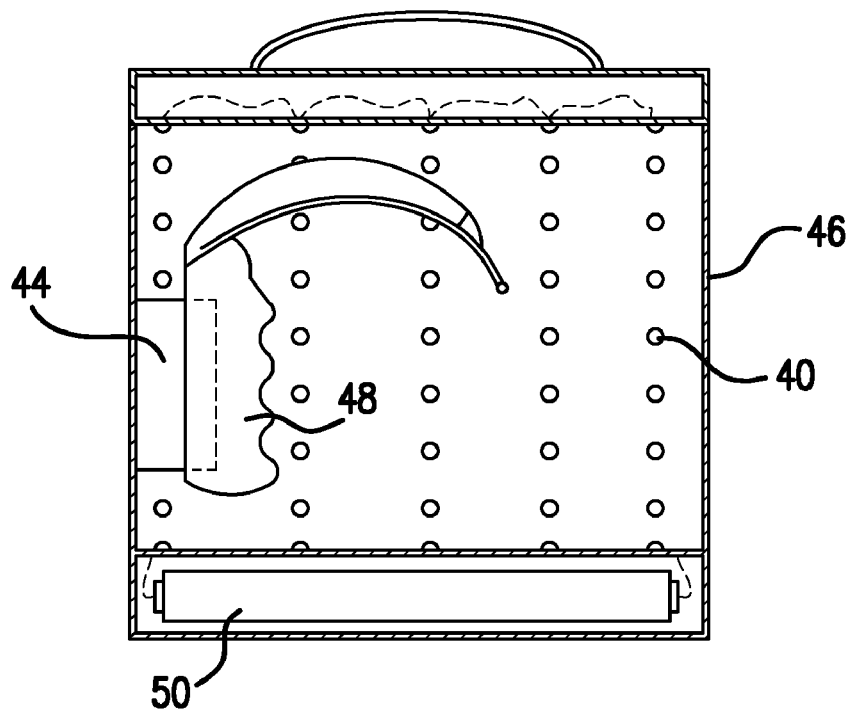
FIG. 7 is a side view of the portable laryngoscope disinfector taken essentially along line 7-7 of FIG. 6.

In the embodiment shown in FIG. 6 and FIG. 7, a mounting base 44 may be affixed to a wall of a portable cabinet 46. The mounting base holds a laryngoscope 48, or alternatively, a bracket may be formed that holds a laryngoscope blade, with another wall holding a laryngoscope handle, when the components are disassembled. Again, the cabinet may have reflective walls for improved efficacy. In use, a laryngoscope is positioned within the cabinet. The top is closed to prevent ultraviolet light from escaping the cabinet. A battery 50 provides power to the ultraviolet light emitting diodes for a sufficient time to adequately disinfect the laryngoscope.

What is claimed is:

1. A laryngoscope disinfector, comprising:
   a cabinet comprising a plurality of ultraviolet radiation emitters;
   a drawer constructed and arranged to engage the cabinet, wherein the drawer comprises a plurality of sides that form the drawer annularly, with the drawer having a top and a bottom that permit ultraviolet radiation to pass through the top and the bottom, wherein a side of the plurality of sides comprises a plurality of hangers, with each of the hangers is constructed and arranged to engage and hold a laryngoscope blade with the laryngoscope blade projecting outwardly and toward a center of the drawer, and a plurality of annular voids that extend from a side of the drawer, each of plurality of annular voids being constructed and arranged to receive and hold a laryngoscope blade extending downwardly from the drawer with the proximal end of the blade positioned above the annular void.

2. A laryngoscope disinfector as described in claim 1, further comprising a pair of spaced apart rollers positioned generally parallel to each other and positioned between a first side of the plurality of sides and an opposite side of the plurality of sides.

3. A laryngoscope disinfector as described in claim 1, further comprising a pair of spaced apart rollers positioned generally parallel to each other and positioned between a first side of the plurality of sides and an opposite side of the plurality of sides, wherein a roller of the pair of spaced apart rollers is connected to a motor.

4. A laryngoscope disinfector as described in claim 1, further comprising a block extending from a side of the drawer wherein the block is constructed and arranged to receive and hold a handle of a laryngoscope.

5. A laryngoscope disinfector as described in claim 1, wherein each of the hangers constructed and arranged to engage and hold a laryngoscope blade with the laryngoscope blade projecting outwardly and toward a center of the drawer comprises a mounting base, two generally parallel arms extending outwardly and toward a center of the drawer and from the mounting base, and a pin that connects on a first end to one of the two generally parallel arms.

6. A laryngoscope disinfector as described in claim 1, wherein a top of the drawer is open.

7. A laryngoscope disinfector as described in claim 1, wherein a bottom of the drawer is open.

8. A laryngoscope disinfector as described in claim 1, wherein a top of the drawer is open and a bottom of the drawer is open.

9. A laryngoscope disinfector as described in claim 1, wherein an annular void of the plurality of annular voids that extend from a side of the drawer constructed and arranged to receive and hold a laryngoscope blade extending downwardly from the drawer with the proximal end of the blade positioned above the annular void is circular.

10. A laryngoscope disinfector as described in claim 1, wherein an annular void of the plurality of annular voids that extend from a side of the drawer constructed and arranged to receive and hold a laryngoscope blade extending downwardly from the drawer with the proximal end of the blade positioned above the annular void is oval.

* * * * *